US012583801B2

(12) United States Patent
Ray et al.

(10) Patent No.: US 12,583,801 B2
(45) Date of Patent: Mar. 24, 2026

(54) PROCESS FOR PRODUCING FERTILIZER FROM A BIOGAS STREAM

(71) Applicant: ThioSolv, LLC, Largo, FL (US)

(72) Inventors: Michael F. Ray, Clearwater, FL (US);
Michael James Ray, St. Petersburg, FL (US)

(73) Assignee: ThioSolv, LLC, Largo, FL (US)

( * ) Notice: Subject to any disclaimer, the term of this patent is extended or adjusted under 35 U.S.C. 154(b) by 529 days.

(21) Appl. No.: 18/184,450

(22) Filed: Mar. 15, 2023

(65) Prior Publication Data

US 2023/0295055 A1 Sep. 21, 2023

Related U.S. Application Data

(60) Provisional application No. 63/320,956, filed on Mar. 17, 2022.

(51) Int. Cl.
*C05C 3/00* (2006.01)
*C12M 1/107* (2006.01)
*C12P 5/02* (2006.01)

(52) U.S. Cl.
CPC ............... *C05C 3/00* (2013.01); *C12M 21/04* (2013.01); *C12P 5/023* (2013.01)

(58) Field of Classification Search
CPC ............ C05C 3/00; C12M 21/04; C12P 5/023
See application file for complete search history.

(56) References Cited

U.S. PATENT DOCUMENTS

| | | | |
|---|---|---|---|
| 3,524,724 A * | 8/1970 | Cox | .......................... C05C 3/00 137/5 |
| 4,001,374 A | 1/1977 | Haese | |
| 5,354,545 A * | 10/1994 | Buisman | ............... B01D 53/52 423/576.2 |
| 7,575,732 B2 | 8/2009 | Anderson et al. | |
| 10,112,145 B1 | 10/2018 | Luo et al. | |
| 2010/0221804 A1* | 9/2010 | Veit | ....................... C12M 21/12 435/165 |
| 2011/0044875 A1 | 2/2011 | Clarkson | |
| 2013/0337513 A1* | 12/2013 | Hickey | .................. C12P 5/023 435/132 |
| 2018/0297845 A1 | 10/2018 | Mengel et al. | |

FOREIGN PATENT DOCUMENTS

| | | | | |
|---|---|---|---|---|
| EP | 0928774 A1 | 7/1999 | | |
| EP | 3838381 A1 | 6/2021 | | |
| WO | WO-2020160998 A1 * | 8/2020 | ............. | C05F 17/15 |

* cited by examiner

*Primary Examiner* — Wayne A Langel
(74) *Attorney, Agent, or Firm* — D'Ambrosio & Menon, PLLC; Usha Menon

(57) ABSTRACT

A process for producing organic fertilizers involves using a waste ammonia stream to capture sulfur dioxide from the oxidation of sulfur or a gas containing sulfur dioxide to make an ammonium bisulfite/sulfite solution. The sulfite solution is used to scrub hydrogen sulfide out of a biogas or other gas stream. The resulting products contain ammonium thiosulfate and ammonium bisulfite/sulfite.

15 Claims, 1 Drawing Sheet

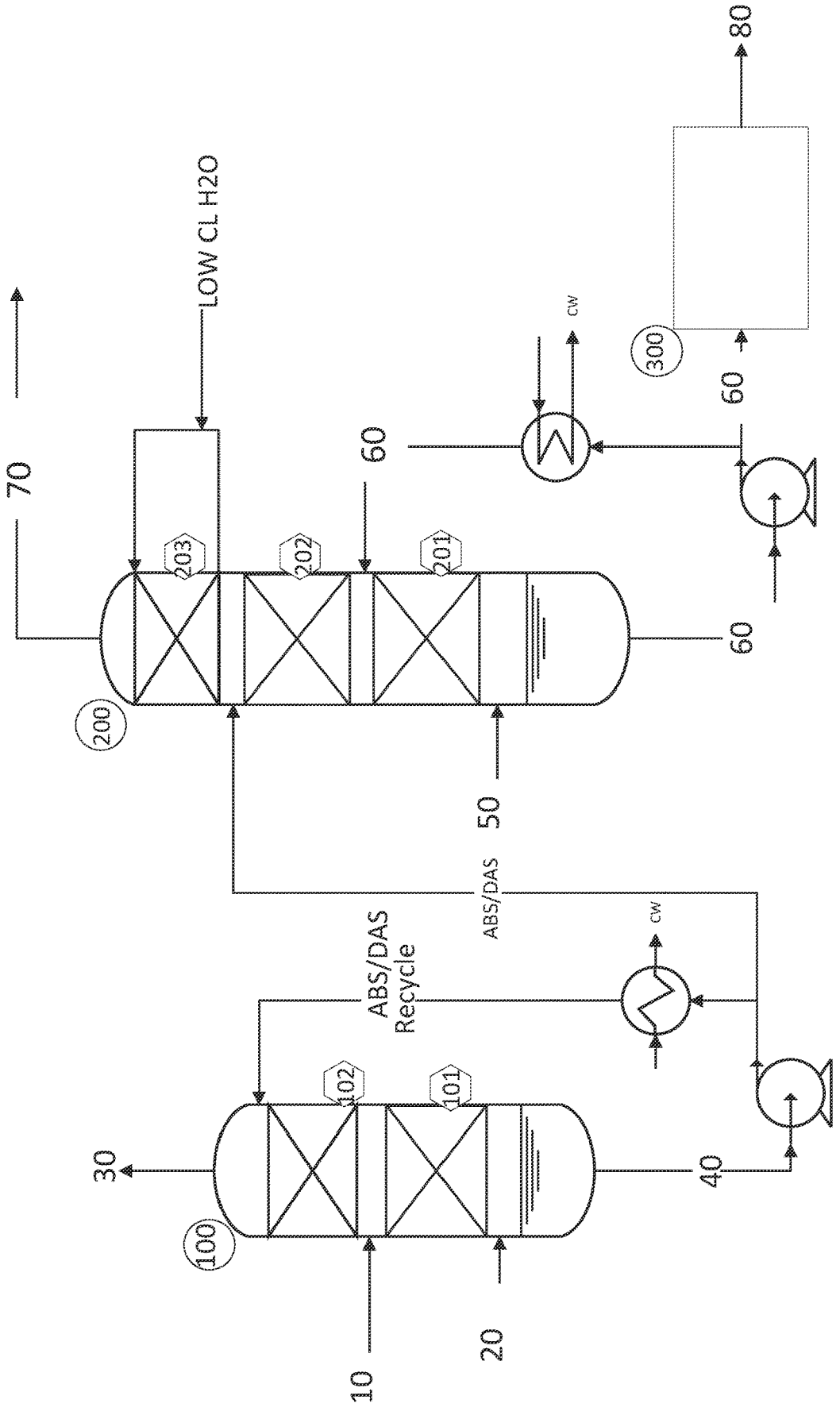

PROCESS FOR PRODUCING FERTILIZER FROM A BIOGAS STREAM

CROSS REFERENCE TO RELATED PATENTS

This application claims priority from U.S. Provisional Patent Application No. 63/320,956 filed on Mar. 17, 2022, the entire disclosure of which is part of the disclosure of the present application and is hereby incorporated by reference in its entirety.

FIELD OF THE INVENTION

The present invention relates to systems and processes for removing hydrogen sulfide from a gas stream. In particular, the present invention relates to a system for removing hydrogen sulfide from a biogas stream while producing ammonium thiosulfate, a high value-added product, useful as a fertilizer.

DESCRIPTION OF THE RELATED ART

Anaerobic digestion is a sequence of processes by which microorganisms break down biodegradable organic material and waste in the absence of oxygen to produce biogas and digestate. Anaerobic digestion can take place in a sealed pond or a reactor vessel containing complex microbial communities. The process is used for industrial or domestic purposes to manage waste or to produce fuels.

Biogas is composed of methane ($CH_4$), which is the primary component of natural gas, at a relatively high percentage (50 to 75 percent), carbon dioxide ($CO_2$), hydrogen sulfide ($H_2S$), water vapor, and trace amounts of other gases. Carbon dioxide lowers the heating value of the biogas, and hydrogen sulfide is a highly corrosive pollutant that is extremely toxic and flammable, especially if exposed to the atmosphere. If the biogas stream is to be used for boilers or other local uses, the carbon dioxide may remain in the biogas. Otherwise, the carbon dioxide and hydrogen sulfide can be removed by conventional systems, such as, an amine system. In conventional amine systems, liquid amine is contacted with the biogas causing carbon dioxide and hydrogen sulfide to be absorbed by the amine. Then the amine is regenerated by stripping carbon dioxide and hydrogen sulfide out, leaving a lean amine that is suitable for recontacting with the biogas. Stripping may be accomplished by heat input or pressure decrease. The degree to which carbon dioxide and hydrogen sulfide is stripped from a rich amine depends on the amount of heat used or the amount the pressure is decreased. Over stripping, or removing more carbon dioxide and hydrogen sulfide than necessary to regenerate amine, may result in an energy penalty. Conversely, government regulations limit the maximum amount of sulfur dioxide that may be generated when gas is combusted, and under stripping, or removing too little acid gas, can result in environmental penalties or unsaleable gas. Lastly, removing sulfur dioxide is a corrosive process and produces an undesirable waste stream.

Ammonia ($NH_3$) in the digestate can also be problematic. A common means of disposal is to air strip $NH_3$ out of the digestate for reaction with sulfuric acid ($H_2SO_4$) to produce an ammonium sulfate (AMS) solution. The low nutrient value of the ammonium sulfate produced and the need to store large quantities of the sulfuric acid and liquid ammonium sulfate makes this process uneconomical.

Therefore, there is a need to convert such lower value-added ammonia streams into higher value-added products, such as organic fertilizers, so that they can be a source of revenue and can increase the environmental benefit of a biogas project or plant.

SUMMARY OF THE INVENTION

According to one or more embodiments of the present invention, a higher value-added ammonium thiosulfate (ATS) solution is produced. ATS can be beneficially used as a fertilizer. The process utilizes an anaerobic digester produced ammonia-containing gas stream and a non-hydrocarbon sourced gas to remove hydrogen sulfide from the biogas. Since the ammonia used to produce the ATS solution is obtained from an organically certified process using an anaerobic digester, the ATS solution can also classified and marketed as an organic product. Furthermore, the product and process are organic since fossil fuel is not consumed.

Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. The foregoing has outlined rather broadly several aspects of the present invention in order that the detailed description of the invention that follows may be better understood.

BRIEF DESCRIPTION OF THE DRAWINGS

FIG. 1 depicts one non-limiting embodiment of a system for removing hydrogen sulfide from a biogas stream and producing ammonium thiosulfate.

DETAILED DESCRIPTION

The present invention relates to systems and processes for removing hydrogen sulfide from a biogas/sour biogas stream. In particular, the present invention relates to a system for removing hydrogen sulfide from a biogas stream while converting low valued ammonia streams into a high valued organic fertilizer, such as, ATS. One example of such a system is depicted in FIG. 1.

It is noted that the components of the embodiment shown in FIG. 1 are not necessarily drawn to scale and emphasis is instead placed upon clearly illustrating the principles of the present invention.

The term "one embodiment" refers to one example of a method or system that can carry out the inventive process described herein. However, it will be apparent to one of ordinary skill in the art that the inventive concepts within the disclosure may be practiced without the specifically described features but be accomplished with a number of alternative components or methods.

As used herein, the terms "column" and "contact zone" can include any combination of towers, columns, trays, vessels, pumps, valves, control systems, and any other equipment known in the art useful in contacting liquids and gases.

An embodiment of the process described herein involves air stripping an aqueous ammonia-containing waste stream from the digestate (produced during anaerobic digestion) at a predetermined temperature to saturate the air with ammonia. The ammonia content in the resulting gas stream can be based on the amount of water in the anaerobic digester (not shown), which is further dependent on the technology, or combination of technologies, used to produce the ammonia. The ammonia content is typically low and can range from 1,500 ppm to 5,000 ppm.

According to another embodiment, an organic fertilizer is produced from two contaminated streams from anaerobic digestion. This involves passing an aqueous ammonia-containing stream from the anaerobic digester through a filter to remove solids followed by boiling ammonia and hydrogen sulfide (contained in the biogas produced during the anerobic digestion) out of the digestate using a sour water stripper. The process liberates the contaminated ammonia and hydrogen sulfide streams by heating the filtered digestate and subsequently condensing the gases in a cooler aqueous solution.

The ammonia-containing gaseous stream produced from the digestate is thus advantageously precluded from being discharged or reused in the digester.

As shown in FIG. 1, an ammonia-containing gas stream 10, produced from the digestate and having a relatively low concentration of ammonia, can be introduced into a first Column 100. A stream of sulfur dioxide ($SO_2$) gas 20 can be added near a first contact zone 101 of Column 100. The ammonia-containing gas stream 10 is circulated through an aqueous solution rich in bisulfite ions near a second contact zone 102. The sulfur dioxide stream 20 can be used to control the sulfite to bisulfite ratio in the circulating solution.

The sulfur dioxide gas stream 20 can be obtained, for instance, from the oxidation of sulfur on site, or it can be a purchased stream of sulfur dioxide. In general, any gas stream rich in sulfur dioxide can be used as stream 20.

The sulfur dioxide is quickly reacted out of Column 100 by maintaining a relatively high pH in the first contact zone 101. A relatively lower pH is maintained in the second contact zone 102 in order to limit the ammonia or sulfur dioxide gases from escaping into the vented gas stream 30. Ammonia, sulfur dioxide, and water react in Column 100 to produce a mixture of ammonium bisulfite (ABS or $NH_4HSO_3$) and diammonium sulfite (DAS or $(NH_4)_2SO_3$) in an aqueous solution. The ratio of ABS and DAS is dependent on the pH of the solution used in the contact zones of Column 100. This ABS/DAS aqueous solution can be sold or used as an intermediate in other processes.

The pH of the two contact zones 101, 102 can be maintained between 4.5 and 7.8, and preferably between 5.5 and 6.5 (where it is again noted that the pH of contact zone 101 is higher than the pH of contact zone 102), to absorb ammonia and to minimize the vapor pressure of sulfur dioxide and ammonia in the solution. The vapor pressure can be further reduced by cooling the circulating solution.

In an alternative embodiment, the contact zones in Column 100 can be reversed such that sulfur dioxide is introduced into the second contact zone while the ammonia-containing stream is introduced into the first contact zone. The respective pH values of the contact zones are accordingly adjusted to limit sulfur dioxide and ammonia emission from vented gas stream 30.

The resulting aqueous solution 40 can exit from Column 100 from the bottom of the column as a liquid mixture of ABS, DAS, and water (also referred to herein as "ABS/DAS solution"). A portion of this solution is taken to a second Column 200 and the remainder is circulated back through the contact zones of Column 100 to add more aqueous ammonia and a sulfite rich solution to the process flow. Simultaneously, the liquid stream re-contacts with sulfur dioxide to substantially increase the concentration of sulfite in solution. The pH of the recirculated or recycled solution is adjusted to below 7.8, with a preferred pH below 6.3, utilizing sulfur dioxide, to further scrub the solution of residual ammonia.

In one embodiment the ABS/DAS solution exiting Column 100 can be used to scrub hydrogen sulfide out of the biogas produced during anaerobic digestion in a contact device to produce ammonium thiosulfate (ATS) which can be used as a fertilizer. The scrubbing can be conducted at a desired pressure, leaving carbon dioxide with the methane in the biogas.

In one or more embodiments, an amine system or other conventional technology is used to remove hydrogen sulfide from a small biogas stream, such that the treated biogas that can be used with commercially produced natural gas. The process uses waste ammonia to capture sulfur dioxide from a burner or as purchased material making an ammonium sulfite solution to subsequently scrub hydrogen sulfide ($H_2S$) out of a biogas or other gas stream. Any remaining carbon dioxide is then vented to the atmosphere.

As shown in FIG. 1, a portion of the ABS/DAS solution 40 is pumped to the second Column 200. There the solution is contacted with a sour biomethane gas 50 (or biogas) that is introduced into Column 200. The biogas 50 can be routed/obtained from the anaerobic digester (or another organic source).

According to one or more embodiments, Column 200 can include multiple contact zones. As shown, in FIG. 1, Column 200 includes three contact zones, namely, 201, 202 and 203. In contact zone 201, the pH is maintained at a higher value than the pH in contact zones 202 and 203 to quickly scrub $H_2S$ out of the biogas. The pH in contact zone 202 is intentionally maintained at a lower value than that in contact zone 201 to limit ammonia, $H_2S$ or $SO_2$ from escaping into the biogas stream. In contact zone 203, water, that is preferably chilled, is contacted with the gas to remove any residual ammonia, $H_2S$ or $SO_2$. Chilled water is further beneficial in lowering the vapor pressure and enhances the capture of ammonia, $H_2S$, and $SO_2$. In an embodiment, the pH of the three contact zones is around 4.5 to 6.3.

Since the outflow solution 40 is aqueous and comprises ammonium bisulfite and ammonium sulfite in their ionic form, the hydrogen sulfide contained in the biogas 50 reacts with the ABS/DAS solution to produce an effluent stream of ammonium thiosulfate (ATS) liquid that can exit from the bottom of the second contact Column 200 as ATS stream 60. The effluent ATS liquid 60 can be transported to a storage unit (or storage area) 300.

Advantageously, carbon dioxide is non-reactive with the ammonium sulfite and ammonium bisulfite in the outflow solution. Therefore, in contrast to most physical and alkaline solvents, the outflow solution 40 selectively captures hydrogen sulfide and rejects the carbon dioxide present in the biogas. Overhead gas stream 70 that leaves the second contact Column 200 has had hydrogen sulfide substantially removed but it can still contain carbon dioxide.

In an exemplary embodiment, the process further involves recycling ATS to beneficially control the nitrogen to sulfur ratio in Contact Zone 201 and to continually enrich the ATS rich liquid in the storage unit 300. The enriched ATS rich liquid can be taken from the storage area 600 to be sold directly as a high-value added fertilizer 80.

A heat exchanger (not shown) can be used to regulate the temperature in Column 200, enhance reaction rates and reduce the amount of hydrogen sulfide reaching contact zone 203. Due to elevated temperature in Column 200, contact zone 203, located near the top of Column 200, can be cooled by introducing chilled water. The chilled water lowers the vapor pressure of the gases, thereby removing any residual ammonia, hydrogen sulfide or sulfur dioxide. Importantly, the stoichiometric ratio of ammonia to hydrogen sulfide is maintained in slight excess of 1:1 to convert all the hydrogen sulfide to ATS in Column 200 and to provide a buffer against any excess hydrogen sulfide in the solution.

In one or more embodiments, the water routed into contact zone 203 has a low chloride content, in the range of 0 to 250 ppm, to prevent any stress corrosion cracking in the stainless-steel portions of the second column.

In an optional embodiment, a portion of the ATS rich stream 60 can be routed to Column 100 to reduce the vapor pressure of sulfur dioxide and ammonia in Column 100 and to increase the ATS content in the circulating solution.

In one or more embodiments, at least two of the contact zones/stages in Column 200 may be combined into one. This can result in cost savings where high removal of hydrogen sulfide is achievable but not essential.

A person skilled in the art would understand that the number of contact zones in the second column (Column 200), the gas velocity, and the recycle rate can be easily manipulated to adapt to various reaction kinetics for the absorption of hydrogen sulfide.

The foregoing describes one or more embodiments for producing organic fertilizers. Advantageously, the embodiments of the invention can use contaminated gaseous streams (containing ammonia and hydrogen sulfide) from an anaerobic digestor to produce a high value added product, namely, ammonium thiosulfate. The present invention, therefore, utilizes an anaerobic digester produced ammonia and a non-hydrocarbon sourced gas to remove hydrogen sulfide from biogas. While many fluid thiosulfate fertilizers are available, ammonium thiosulfate (ATS) is the most widely used fluid fertilizer that contains sulfur. It contains sulfur dioxide, elemental sulfur, and aqueous ammonia in a liquid format that serves as an effective source of sulfur and nitrogen to crops. The present invention produces significant amounts of an organic ATS fertilizer that meets the Principles of Organic Agriculture and can be used for commercial organic agriculture.

Organic fertilizers are fertilizers that are produced from natural sources as opposed to synthetic fertilizers that are man-made, inorganic fertilizers. Organically derived fertilizers stimulate beneficial soil microorganisms and improve the structure of the soil. Soil microbes play a key role in converting organic fertilizers into soluble nutrients that can be absorbed by plants at a rate they can use, thereby promoting stronger root growth for better disease and insect resistance. Furthermore, organic fertilizers that meet the Principles of Organic Agriculture can be used for commercial organic agriculture. ATS in particular inhibits the conversion of ammonia in the soil to nitrate thereby allowing the applied ammonia based fertilizer to be better utilized by the plant.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

The invention claimed is:

1. A process for producing an organic fertilizer, comprising:

introducing a stream of sulfur dioxide into a first column;

routing an ammonia-containing gas stream into the first column, wherein the ammonia-containing gas stream is circulated through an aqueous solution containing bisulfite ions in the first column, and further wherein the ammonia-containing gas stream reacts with the sulfur dioxide and the aqueous solution containing bisulfite ions to produce an aqueous solution comprising ammonium bisulfite and diammonium sulfite;

wherein the first column contains at least two contact zones, and wherein the sulfur dioxide is introduced near a first contact zone and the ammonia-containing gas stream is introduced near a second contact zone, and further comprising maintaining a higher pH in the first contact zone and a lower pH in the second contact zone;

routing a portion of the aqueous ammonium bisulfite and diammonium sulfite solution to a second column;

introducing a biogas stream into the second column, wherein the biogas stream comprises hydrogen sulfide; and contacting the routed aqueous ammonium bisulfite and diammonium sulfite solution and biogas stream in the second column to substantially scrub the hydrogen sulfide from the biogas stream and produce an effluent stream containing aqueous ammonium thiosulfate.

2. The process according to claim 1, wherein the second column comprises a plurality of contact zones.

3. The process according to claim 2, wherein the second column includes three contact zones, and wherein the pH of a first contact zone in the second column is maintained at a higher value than the pH in the second and third contact zones to quickly scrub hydrogen sulfide out of the biogas stream.

4. The process according to claim 3, wherein chilled water is circulated into a third contact zone.

5. The process according to claim 4, wherein the chilled water has a low chloride content in the range of 0 to 250 ppm to prevent corrosion of the column.

6. The process according to claim 2, wherein the pH of each contact zone in the second column is around 4.5 to 6.3.

7. The process according to claim 1, wherein a portion of the aqueous ammonium thiosulfate is recirculated through the second column.

8. The process according to claim 7, wherein another portion of the aqueous ammonium thiosulfate is routed to a storage unit.

9. The process according to claim 1, wherein the ammonia-containing gas stream is obtained from an anaerobic digestate.

10. The process according to claim 1, wherein the ammonia-containing gas stream is produced from a sour water stripper or steam stripper.

11. The process according to claim 1, wherein the pH of the first and second contact zones is in the range of 5.5 to 6.5.

12. The process according to claim 1, wherein another portion of the aqueous ammonium bisulfite and diammonium sulfite solution is circulated back into the first column.

13. The process according to claim 1, wherein the biogas is produced during an anaerobic digestion reaction, and wherein the biogas further comprises methane and carbon dioxide.

14. The process according to claim 1, wherein a stoichiometric excess of ammonia to hydrogen sulfide is maintained in the second column.

15. The process according to claim 1, wherein the process utilizes an anaerobic digester produced ammonia-containing gas stream and a non-hydrocarbon sourced gas to remove hydrogen sulfide from the biogas.

* * * * *